United States Patent
Mathews et al.

[11] Patent Number: 6,133,994
[45] Date of Patent: Oct. 17, 2000

[54] TESTING DEVICE FOR LIGHT EMITTERS

[75] Inventors: Geoffrey Richard Mathews, Llangwm; Anthony John Flint, Cardiff, both of United Kingdom

[73] Assignee: The Electrode Company Limited, Gwent, United Kingdom

[21] Appl. No.: 09/138,875

[22] Filed: Aug. 24, 1998

[30] Foreign Application Priority Data

Aug. 23, 1997 [GB] United Kingdom .................. 9717858

[51] Int. Cl.[7] ............................................... G01N 33/48
[52] U.S. Cl. ............................................................ 356/41
[58] Field of Search ................................ 356/39, 40, 41, 356/42, 243; 250/252.1; 600/330

[56] References Cited

U.S. PATENT DOCUMENTS

| | | | |
|---|---|---|---|
| 4,061,925 | 12/1977 | van der Gaag | 250/553 |
| 4,611,116 | 9/1986 | Batt | 250/239 |
| 4,834,532 | 5/1989 | Yount | 356/41 |
| 5,784,151 | 7/1998 | Miller et al. | 356/41 |
| 5,823,950 | 10/1998 | Diab et al. | 600/310 |

FOREIGN PATENT DOCUMENTS

| | | |
|---|---|---|
| 0 329 196A2 | 8/1983 | European Pat. Off. . |
| 0 104 772A2 | 4/1984 | European Pat. Off. . |
| 207 984 | 3/1984 | Germany . |
| WO96/41138 | 12/1996 | WIPO . |

*Primary Examiner*—Frank G. Font
*Assistant Examiner*—Michael P. Stafira
*Attorney, Agent, or Firm*—David P. Gordon; David S. Jacobson; Thomas A. Gallagher

[57] ABSTRACT

A device for testing a pulse oximetry probe includes means for receiving an output signal dependent on the wavelength of light emitted by a light emitter of the probe, and for determining, from this output signal, an accuracy figure for the blood oxygen indication of the probe.

22 Claims, 3 Drawing Sheets

TESTING DEVICE FOR LIGHT EMITTERS

BACKGROUND OF THE INVENTION

1. Field of the Invention

The present invention relates to a device for testing light-emitters, particularly the light emitters of pulse oximetry probes.

2. State of the Art

Pulse oximetry is a non-invasive technique for measuring the oxygen content of a subject's blood and is in common usage throughout the world. A pulse oximeter consists of a probe connected by a length of cable to a monitor which includes a display, from which the oxygen content of the subject's blood can be read. Typically, the probe includes two light emitting diodes (LED's) of different wavelengths, and a photodiode: the probe is usually applied to the subject's finger, arranged for the light from the respective LED's to be transmitted through the finger tissues to the photodiode. A ratio derived from photodiode output signals, when receiving light from the different LED's, is used to provide a measure of the blood oxygen content: more specifically, the ratio of the pulsatile component to the non-pulsatile component of the photodiode output when receiving the red light is determined, and a similar ratio is determined for the corresponding components of the photodiode output when receiving the infra red light; then the final ratio is formed between these respective ratios.

Most commonly, pulse oximeter probes are reusable and are accordingly used until they fail mechanically, at which time it becomes self-evident that they are unsuitable for further use. In the meantime, however, the accuracy of the probe is rarely (if ever) checked, because the only means known for doing so are complex and therefore relatively expensive.

We have now found that the components of pulse oximeter probes commonly deteriorate with age: this can lead to a decrease in accuracy. We have also found that "remanufactured" probes are often in use in hospitals, some of which have had replacement components of the wrong specification fitted to them, with the result that these probes are inaccurate.

SUMMARY OF THE INVENTION

We have now devised a device for testing a pulse oximetry probe, in order to overcome the problems outlined above.

In accordance with the present invention, there is provided a device for testing a pulse oximetry probe, the device including means for producing or receiving an output signal dependent on the wavelength of light emitted by at least one light emitter of the probe, and for determining, from said output signal, an accuracy figure for the blood oxygen indication of the probe.

Thus, we have found that the main cause of inaccuracy of pulse oximetry probes is due to LED's which emit light at incorrect wavelengths, either because the wavelength has changed with the age of the LED or because an LED of incorrect wavelength has been fitted as a replacement.

The testing device of the present invention accordingly tests the probe in respect of the wavelength of the light emitted by at least one of the light emitters of the probe. Preferably the testing device tests the probe in respect of the wavelength of its red emitter, but more preferably tests the probe in respect of the wavelengths of both its red and infra red emitters.

In order to determine the accuracy figure for the blood oxygen indication of the probe, preferably the testing device comprises a memory which stores data defining the accuracy figure for different values of the wavelength-dependent signal or signals. Thus, once this signal or these signals are provided, the signal or signals are used to address the memory and so output the accuracy figure. Preferably the accuracy figure is provided as a percentage deviation which the blood oxygen indication will be from its correct value. The testing device may be arranged to give a "pass" indication if the accuracy figure (whether positive or negative) is below a predetermined percentage (e.g. ±2%) and otherwise give a "fail" indication.

The testing device may be arranged to measure a first output signal of a photodetector positioned to receive light directly from a light emitter of the probe, and to measure a second output signal of the same or another photodetector positioned to receive light from the same light emitter through a filter. The device is then further arranged to determine a ratio of these first and second output signals and, from stored data representing the transmission characteristic of the filter, provide the aforementioned signal which is dependent on the wavelength of the light emitter.

Preferably the testing device is arranged to form, in a similar manner, wavelength-dependent signals in respect of two emitters (red and infra red emitters) of the probe.

The testing device may use the photodetector of the probe itself to provide the first and second output signals required for the or each emitter. In particular, the photodetector output may be measured without the filter inserted between the probe light emitter and the photodetector, and separately with the filter inserted.

Alternatively, an auxiliary unit may be provided for insertion into the probe, this auxiliary unit having one or more photodetectors to pick up the light from the or each emitter of the probe, the photodetector or photodetectors of the auxiliary device providing the output signals required for processing.

In a simplified arrangement, light from the red emitter of the probe is passed through a filter to a photodetector and the output signal of the photodetector determined. Likewise, light from the infra red emitter of the probe is passed through a filter to the same (or a different) photodetector and the output signal of the photodetector is determined. A ratio of these two signals, respectively dependent on the actual wavelengths of light emitted by the red and infra red emitters, is then determined. Alternatively, a first value is formed, as the ratio of the photodetector outputs for light received from the red emitter respectively through the filter and directly (no filter), a second value is formed in similar manner with respect to the infra red emitter, and a ratio of these first and second values is formed. It will be appreciated that for a given probe, the final ratio should in each case be constant: any deviation from the constant value represents an inaccuracy in the probe output. As previously described, the testing device may be arranged to determine an accuracy figure for the blood oxygen indication of the probe.

Although the invention has been described for use in testing pulse oximetry probes, its principles may be used generally for testing light emitters in respect of the wavelengths of light which they emit.

Thus, also in accordance with the present invention, there is provided a device for testing a light emitter, the device comprising a photodetector for receiving light from said light emitter through a filter to produce an output signal, and means for processing said output signal to determine any deviation of said light from a predetermined wavelength.

As previously described, the device may be arranged to measure a first output signal of the photodetector when receiving light directly from the light emitter, and to measure a second output signal of the same or another photodetector when receiving light from the light emitter through the filter. The device is then further arranged to determine a ratio of these first and second output signals and, from stored data representing the transmission characteristic of the filter, provide a signal which is dependent on the wavelength of the light from the light emitter. This signal may be processed to indicate the actual wavelength of the light emitter and/or an accuracy figure for the light emitter or any measuring device in which it is used.

Instead, also as previously described, the output of the photodetector, for light received from the emitter via the filter, may be compared to the photodetector output for light received direct from the emitter, in order to produce a ratio value for further processing to determine the deviation of the emitted light from a predetermined wavelength (i.e. its rated wavelength).

In all of the above described arrangements the or each emitter may further be checked using two filters, one having a negative gradient in its transmission characteristic at the rated wavelength of the emitter, and the other having a positive gradient in its transmission characteristic at that wavelength. In this case, the testing device tests the emitter using one filter and then tests it again using the other filter: these two successive tests should provide wavelength measurements which agree with one another; however, if they differ from one another by more than a predetermined amount (typically as a result of the emitter output having become excessively broad in bandwidth), then the device may indicate a "fail".

Where the light emitter emits light of a narrow bandwidth, the use of the true transmission characteristic of the filter will provide an accurate determination of the wavelength (or peak wavelength) of the emitted light. However, if the light emitter emits light of a relatively broad bandwidth, use of the true transmission characteristic may give an inaccurate determination of the peak or median wavelength of the emitted light. It is however possible to form a modified transmission characteristic from the true transmission characteristic of the filter, which will then give a more accurate determination of the peak or median wavelength of a light beam of relatively broad bandwidth: the degree of modification required to the true transmission characteristic will vary according to the bandwidth of the light beam. The modified transmission characteristic may also take account of the spectral characteristic of the light beam.

In accordance with the present invention, the data stored for the transmission characteristic for one of the filters (particularly for the infra red LED, which is usually of much broader bandwidth than the red LED) is modified from the true characteristic data, to compensate for the expected broad bandwidth of the light from the LED.

Alternatively or in addition, the testing device may be arranged to determine the bandwidth of the or each LED and positive gradient in their transmission characteristics, as described previously: the device stores a number of sets of data representing modified transmission characteristics, appropriate for different bandwidths of light beams. The device selects the set of data appropriate for the measured bandwidth, in order to determine more accurately the peak or median wavelength of the light beam.

Embodiments of the present invention will now be described by way of examples only and with reference to the accompanying drawings.

DETAILED DESCRIPTION OF THE PREFERRED EMBODIMENTS

Figure 1:
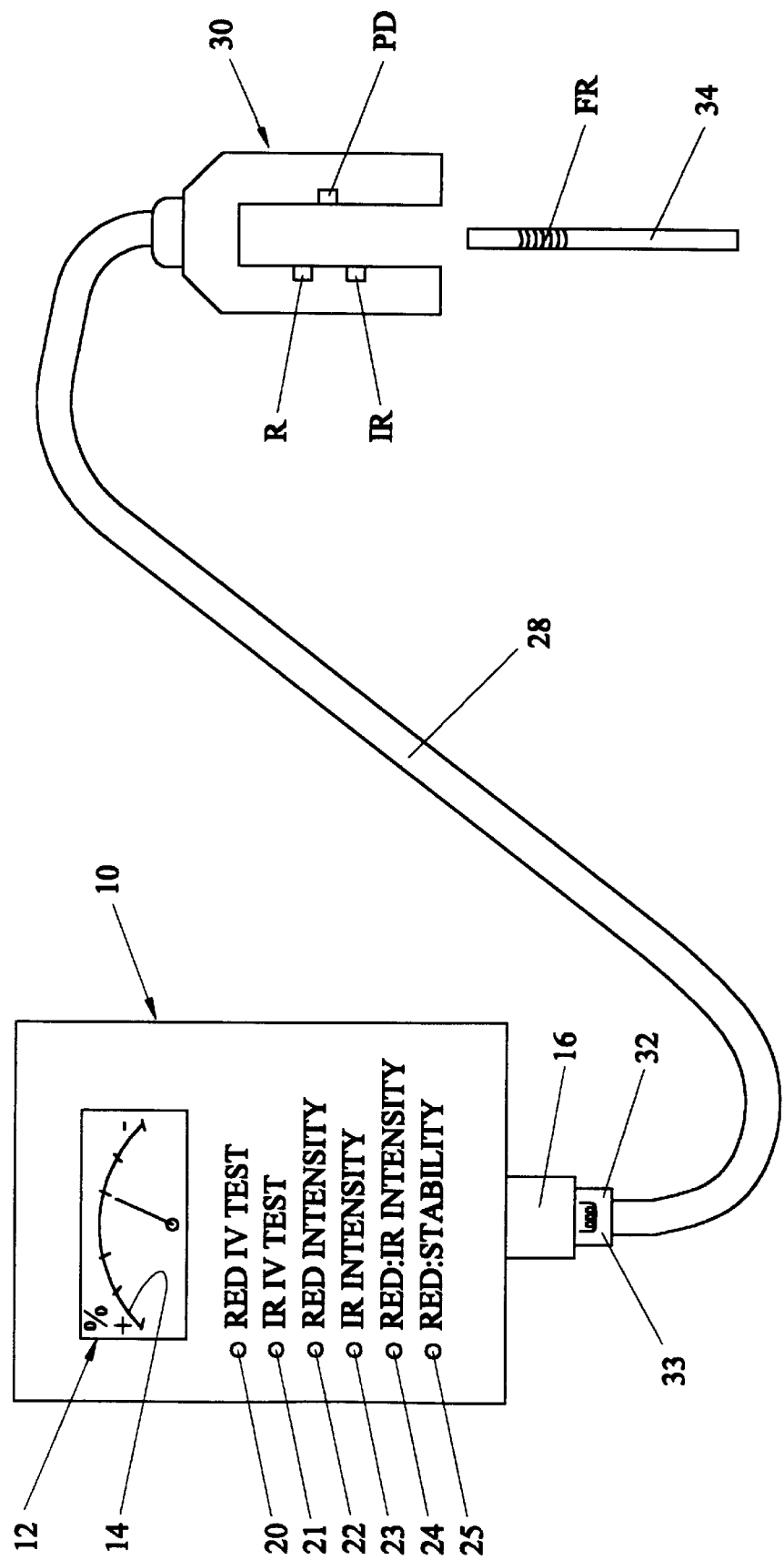
FIG. 1 is a schematic diagram of a testing device in accordance with the invention, shown connected to a typical pulse oximetry probe.

Referring to FIG. 1, there is shown a testing device 10 for use in testing pulse oximetry probes. The testing device 10 is a hand-held device, the casing of which houses the electronic circuit of the device and batteries for powering the circuit. The front face of the casing is provided with a visual display 12 and with a series of indicator lights 20–25, the purpose of which will be described below. FIG. 1 also shows a pulse oximetry probe 30 to be tested, connected to the testing device 10 by a cable 28.

As shown diagrammatically in FIG. 1, the pulse oximetry probe 30 is in the form of a clip for applying to the subject's finger. In one limb of the device, two light emitting diodes R and IR are mounted: in the opposite limb of the device, a photodiode PD is mounted. The LED R is such that, when energised, it emits light which has a narrow peak in the red part of the light spectrum; the LED IR is such that, when energised, it emits light which has a narrow peak in the infra red part of the spectrum.

The testing device 10 is firstly used without any item inserted into the probe clip. The testing device 10 is arranged to feed a constant current to each of the LED's R and IR in turn, and in each case to measure the voltage across the component. If the measured voltage lies within a predetermined range in each case, the respective indicator lights 20,21 are energised. Also in each case, the device 10 measures the output signal from the photodiode PD is measured: if the output signal lies within a predetermined range in each case, the respective indicator lights 22,23 are energised. Further, the device determines the ratio of the outputs from the photodiode PD (when the respective LED's R and IR are energised): if this ratio is within a predetermined range, indicator light 24 is energised.

Next a filter holder 34 is inserted into the space between the two limbs of the probe 30, to position a red filter FR between the red LED R and the photodiode PD. The testing device 10 now feeds its constant current through the red LED R and the output signal from the photodiode PD is measured. Then a second filter holder (not shown) is inserted into the probe 30 to position an infra red filter between the infra red LED IR and the photodiode: the infra red LED IR is fed with its constant current and the photodiode output is measured.

Figure 2:
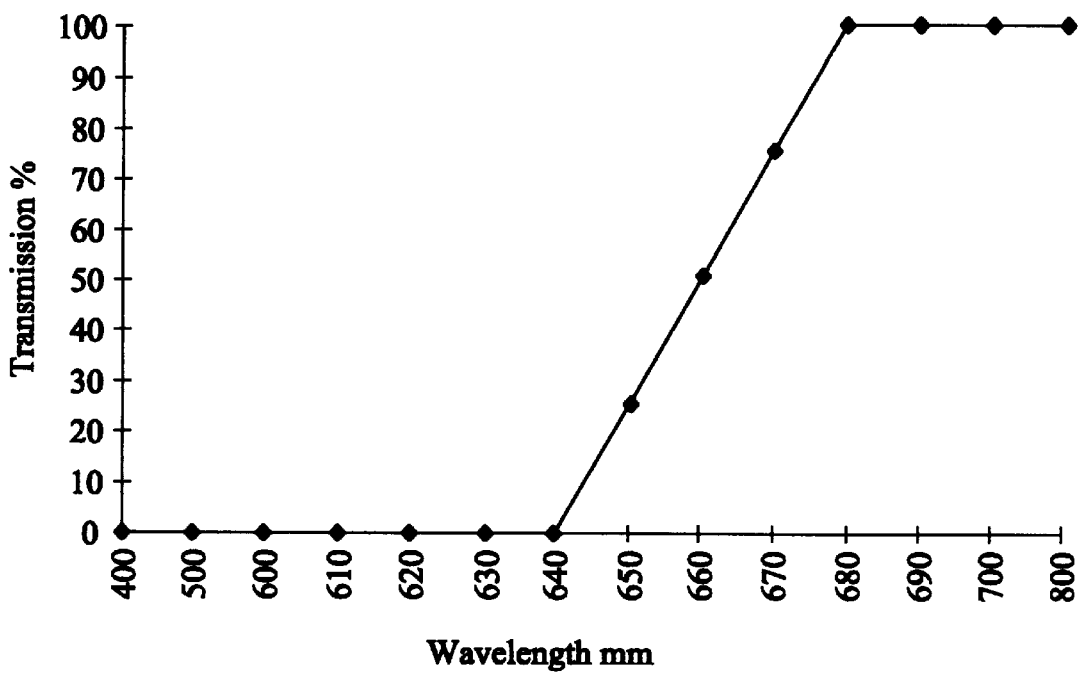
FIGS. 2 and 3 are idealised transmission characteristics for typical red and infra red filters for use with the testing device.
Figure 3:
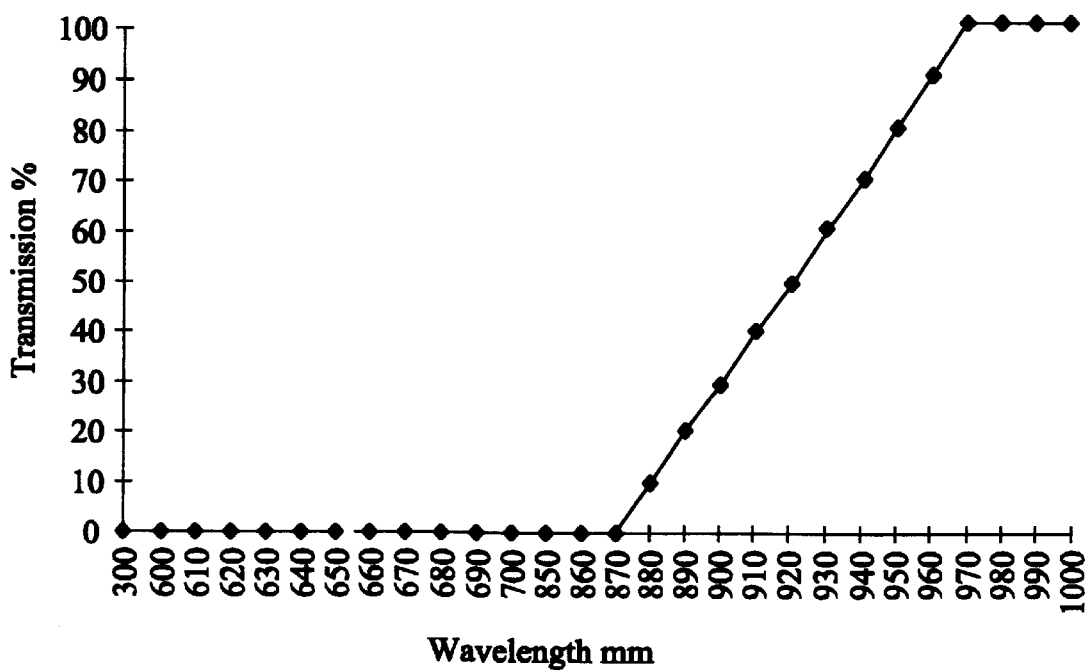

For each LED R and IR, the testing device 10 calculates the ratio of the photodiode output signal measured when the filter is present, to the photodiode output signal measured when the filter is absent. FIGS. 2 and 3 show idealised transmission characteristics for red and infra red filters, respectively. The testing device 10 stores in its memory data representing the transmission characteristics for the filters FR and FIR which are used. For each LED, the testing device compares the calculated ratio of the two photodiode outputs (with filter and without filter) against the respective stored transmission characteristic, in order to determine the actual wavelength of light emitted by the LED.

Referring to the transmission characteristic shown in FIG. 2, at 630 nm the ratio would be zero, at 660 nm it would be 50%, at 670 nm it would be 80% and above 680 nm it would be 100%. Accordingly, once the actual ratio of photodiode output signals for the red LED R is calculated, the wavelength of that red LED can be determined between 640 nm and 680 nm. Likewise, referring to the transmission characteristic shown in FIG. 3, once the actual ratio of photodiode output signals for the infra red LED IR is calculated, the wavelength of that infra red LED can be determined within the range 870 nm to 970 nm.

In this way, the testing device 10 is arranged to determine the actual wavelength emitted by each of the two LED's of the pulse oximetry probe 30. At least for the red LED R, the wavelength value may be displayed in the visual display 12, and the deviation from the rated wavelength may also be displayed.

Furthermore, the testing device 10 is arranged to calculate and display a percentage accuracy value for the blood oxygen content which the probe will indicate, when in normal use. Thus, the testing device 10 stores data defining the accuracy of the probe for different deviations of the LED wavelengths from their rated wavelength values. By addressing the internal memory which stores this data, the testing device is able to determine an accuracy value for the probe: this may be indicated on a scale 14 on the visual display 12.

The testing device 10 may also be arranged to run a test to check the stability in wavelength of light emitted by the red LED R (or by each of the red and infra red LED's). For this, the LED is energised continuously over a period of time, e.g. 5 minutes, and at intervals within that period the intensity and/or wavelength of emitted light is determined. If the LED output remains stable within predetermined limits, then an indicator light 25 is energised.

Preferably the filter holders e.g. 34 are carried by a projection extending from the body of the testing device 10. Preferably the filter holders are independently movable and the testing device 10 is arranged so that, once the probe 30 is clipped onto the testing device projection and a "start" key of the unit is operated, the testing device 10 automatically runs its tests with both filter holders retracted and then advances the filter holders in turn, to interpose their respective filters between the LED's and the photodiode, and runs its remaining tests.

In one modification, each filter may be an electrically or electronically activated filter (e.g. a liquid crystal device), so that it can be switched between two different transmission states. In another modification, a single filter may be used for both LED's, the filter having a significant gradient (positive or negative) in its transmission characteristic, in each of the red and infra red parts of the spectrum.

The testing device 10 is preferably arranged so that it can test a number of different models of pulse oximetry probes. For this purpose, the testing device is required to recognise the particular model of probe which is connected to it, so that it can then select, from its memory, the characteristic data appropriate to that probe.

For this purpose, the testing device 10 may be provided with a plurality of different connector sockets e.g. 16, to receive the connector plugs e.g. 32 at the free ends of the cables of different manufacturers' probes (the plugs used by different manufacturers being of different shapes or sizes). In some cases, a manufacturer provides an identifying resistor (indicated at 33 in FIG. 1) in the connector plug, the resistor value varying according to the rated wavelength of the red LED of the probe: for these cases, the testing device 10 is arranged to pass a constant current through the identifying resistor of the plug (when inserted into the test unit socket) and measure the voltage in order to identify the probe.

The connector socket of the testing device 10 may be arranged for connection of probes having connector plugs of different shapes or sizes, through the use of different conversion leads. In this case, a different conversion lead is used for each different model of probe, and an identifying resistor is then included in the plug of the conversion lead, to identify the model of probe for which it is suited.

Figure 4:
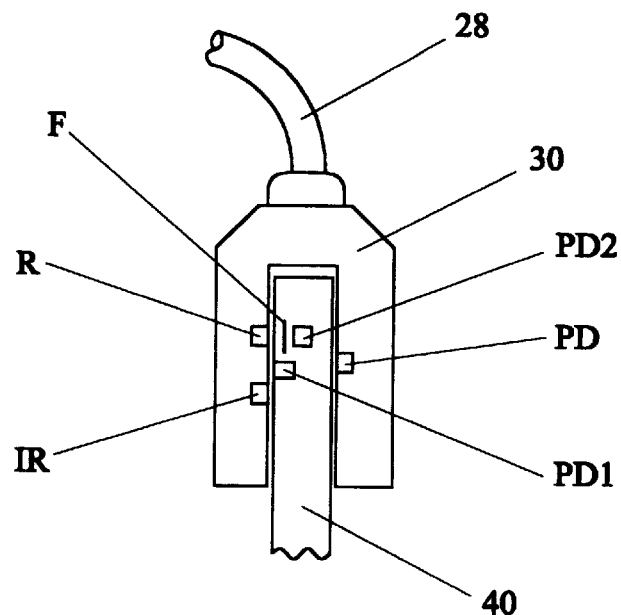
FIG. 4 is a schematic diagram showing an auxiliary unit inserted into a pulse oximetry probe, for use with the testing device.

Whilst the testing device 10 which has been described uses the photodiode PD of the probe 30 to test its LED'S, an auxiliary unit 40 as shown in FIG. 4 may be inserted into the probe, to provide independent testing of the probe LED's. The unit 40 may be provided as a projecting part of the testing device 10. Thus, the unit 40 includes two photodiodes PD1 and PD2. Photodiode PD1 is able to receive light directly from each of the probe LED's R and IR whilst photodiode PD2 is able to receive light from the red LED R only through a filter F. The LED's R and IR of the probe 30 are energised in turn by the testing device, and the corresponding output signals from the photodiode PD1 are measured to determine whether they lie within predetermined ranges. Also, the ratio of the output of photodiode PD1 (for the red LED) to the output of the photodiode PD2 is calculated by the testing device and compared with the filter transmission characteristic, as described previously, to determine the actual wavelength of light emitted by the red LED of the probe, and further to determine the accuracy figure for the probe.

In a modification, the auxiliary unit 40 may comprise a first photodiode, for checking the output of each of the two LED's of the probe in turn, a second photodiode provided with an appropriate filter to check the output of the red LED, and a third photodiode with an appropriate filter to check the output of the infra red LED. Alternatively, as previously noted, both LED'S may be checked using a filter having a significant gradient, in its characteristic, in both the red and infra red parts of the spectrum (in which case one photodiode, with filter, and one photodiode, without filter, are provided).

Figure 5:
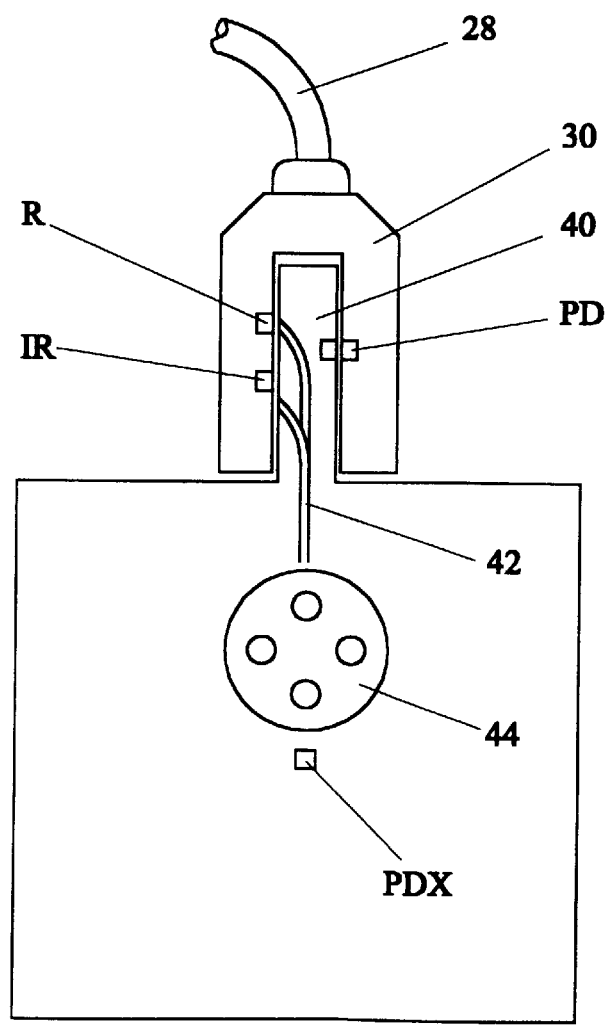
FIG. 5 is a schematic diagram showing a further modification to the device.

Referring to FIG. 5, there is shown a further modification to the arrangement shown in FIG. 4. The auxiliary unit 40 is provided as a projection of the testing device 10, as previously described, but one or more optical fibres 42 extend through the projecting unit 40 to carry the light emitted by the LED's of the pulse oximetry probe. Within the device, a filter wheel 44 is positioned between the inner end of the optical fibre 42 and a photodetector PDX. In the example shown, the filter wheel has four windows, one with no filter, a second with a red filter, a third with an infra red filter, and a fourth with a different infra red filter. By rotation of the filter wheel to position its different windows between the end of the optical fibre and the photodetector PDX, the photodetector can be used to measure the output of each LED of the probe both directly and via its respective filter, the measured outputs being used as described above for testing the probe. The different infra red filters are used for different models of probe. The projecting unit 40 also includes an LED T for testing the photodiode PD of the probe 30.

It will be appreciated that a testing device of relatively simple form has been described, which can be used with ease to make a reliable test of pulse oximetry probes: such a facility has not hitherto been available. However, also as previously described, whilst the principles of the invention may be used for testing pulse oximetry probes, they also may be used generally for testing light emitting devices (whether as discrete devices or as components of measurement instruments).

What is claimed is:

1. A device for testing a pulse oximetry probe, the device including means for producing or receiving an output signal which varies in proportion to any deviation from a predetermined value in the wavelength of light emitted by a light emitter of the probe, and a means for determining, from said output signal, an accuracy figure for the blood oxygen indication of the probe.

2. A device as claimed in claim 1, arranged to test the probe in respect of the light emitted by a red emitter thereof.

3. A device as claimed in claim 1, arranged to test the probe in respect of the light emitted by each of a red emitter and an infra red emitter thereof.

4. A device as claimed in claim 1, further comprising a memory which stores data defining said accuracy figure for different values of said output signal.

5. A device as claimed in claim 4, arranged to provide said accuracy figure as a percentage deviation of the blood oxygen indication of the probe from its correct value.

6. A device as claimed in claim 1, arranged to give a "pass" or "fail" indication according to the value of said accuracy figure.

7. A device as claimed in claim 1, arranged to measure a first output signal of a photodetector positioned to receive light directly from a light emitter of the probe, to measure a second output signal of the same or another photodetector positioned to receive light from the same emitter through a filter, then to determine said output signal from said first and second output signals.

8. A device as claimed in claim 7, arranged to store data defining the transmission characteristic of said filter, said output signals and said transmission characteristic data being used to determine said output signal.

9. A device as claimed in claim 8, in which said stored transmission characteristic is modified from the true filter transmission characteristic, to compensate for a relatively broad bandwidth of the light emitted by the light emitter.

10. A device as claimed in claim 9, arranged to determine the bandwidth of the received light and to select, in accordance therewith, one set of modified transmission characteristic data, from a number of sets of such data, for the filter being used to determine said output signal for said received light.

11. A device as claimed in claim 7, including an auxiliary unit for insertion into the probe, the auxiliary unit including said photodetector or photodetectors.

12. A device as claimed in claim 7, including an auxiliary unit for insertion into the probe, the auxiliary unit including a light guide to carry light from the or each light emitter to one or more photodetectors.

13. A device for testing a light emitter, the device comprising a photodetector for receiving light emitted by said light emitter through a filter to produce an output signal, and means for processing said output signal to determine the degree of any deviation in the wavelength of said light from a predetermined value.

14. A device as claimed in claim 13, arranged to measure a first output signal of said photodetector when receiving light directly from the light emitter, to measure a second output signal of the same or another photodetector when receiving light from the light emitter through said filter, and to determine a wavelength-dependent signal from said first and second output signals.

15. A device as claimed in claim 14, to test the or each emitter using two filters in succession, one filter having a negative gradient in its transmission characteristic at the rated wavelength of the emitter and the other filter having a positive gradient in its transmission characteristic at said rated wavelength, and arranged to compare the successive test results.

16. A device for testing a pulse oximetry probe, the device including means for producing or receiving an output signal dependent on the wavelength of light emitted by at least one light emitter of the probe, and for determining, from said output signal, an accuracy figure for the blood oxygen indication of the probe, wherein the device is arranged to measure a first output signal of a photodetector positioned to receive light directly from a light emitter of the probe, to measure a second output signal of the same or another photodetector positioned to receive light from the same emitter through a filter, and to determine said wavelength-dependent output signal from said first and second output signals.

17. A device as claimed in claim 16, arranged to store data defining the transmission characteristic of said filter, said output signals and said transmission characteristic data being used to determine said output signal.

18. A device as claimed in claim 16, including an auxiliary unit for insertion into the probe, the auxiliary unit including said photodetector or photodetectors.

19. A device as claimed in claim 16, including an auxiliary unit for insertion into the probe, the auxiliary unit including a light guide to carry light from the or each light emitter to one or more photodetectors.

20. A device for testing a light emitter, the device comprising a photodetector for receiving light from said light emitter through a filter to produce an output signal, and means for processing said output signal to determine any deviation of said light from a predetermined wavelength value, wherein said device is arranged to measure a first output signal of said photodetector when receiving light directly from the light emitter, to measure a second output signal of the same or another photodetector when receiving light from the light emitter through said filter, and to determine a wavelength-dependent signal from said first and second output signals.

21. A device as claimed in claim 20, to test the or each emitter using two filters in succession, one filter having a negative gradient in its transmission characteristic at the rated wavelength of the emitter and the other filter having a positive gradient in its transmission characteristic at said rated wavelength, and arranged to compare the successive test results.

22. A method for determining the stability of a wavelength produced by a light emitter, comprising the steps of:
   a) energizing the light emitter continuously for a period of time;
   b) measuring a wavelength of light emitted from the light emitter at intervals over said period of time; and
   c) comparing wavelength measurements taken over the period of time to determine stability of the light emitter.

* * * * *